US00PP26323P3

(12) United States Plant Patent
Suphachadiwong

(10) Patent No.: US PP26,323 P3
(45) Date of Patent: Jan. 19, 2016

(54) *VANDA* PLANT NAMED 'SPCDW1209'

(50) Latin Name: ***Vanda* hybrid**
Varietal Denomination: SPCDW1209

(71) Applicant: Thumrong Suphachadiwong, Chonburi (TH)

(72) Inventor: Thumrong Suphachadiwong, Chonburi (TH)

(73) Assignee: Suphachatawong Innovation (TH)

( * ) Notice: Subject to any disclaimer, the term of this patent is extended or adjusted under 35 U.S.C. 154(b) by 173 days.

(21) Appl. No.: 13/987,935

(22) Filed: Sep. 16, 2013

(65) Prior Publication Data

US 2014/0082797 P1 Mar. 20, 2014

(30) Foreign Application Priority Data

Sep. 17, 2012 (QZ) ..... PBR 20121963

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

*Primary Examiner* — June Hwu
(74) *Attorney, Agent, or Firm* — Cassandra Bright

(57) ABSTRACT

A new and distinct *Vanda* cultivar named 'SPCDW1209' is disclosed, characterized by grey-orange flower color and bright green leaves. The new variety is a *Vanda*, typically produced as an indoor ornamental plant.

2 Drawing Sheets

Figure 1:
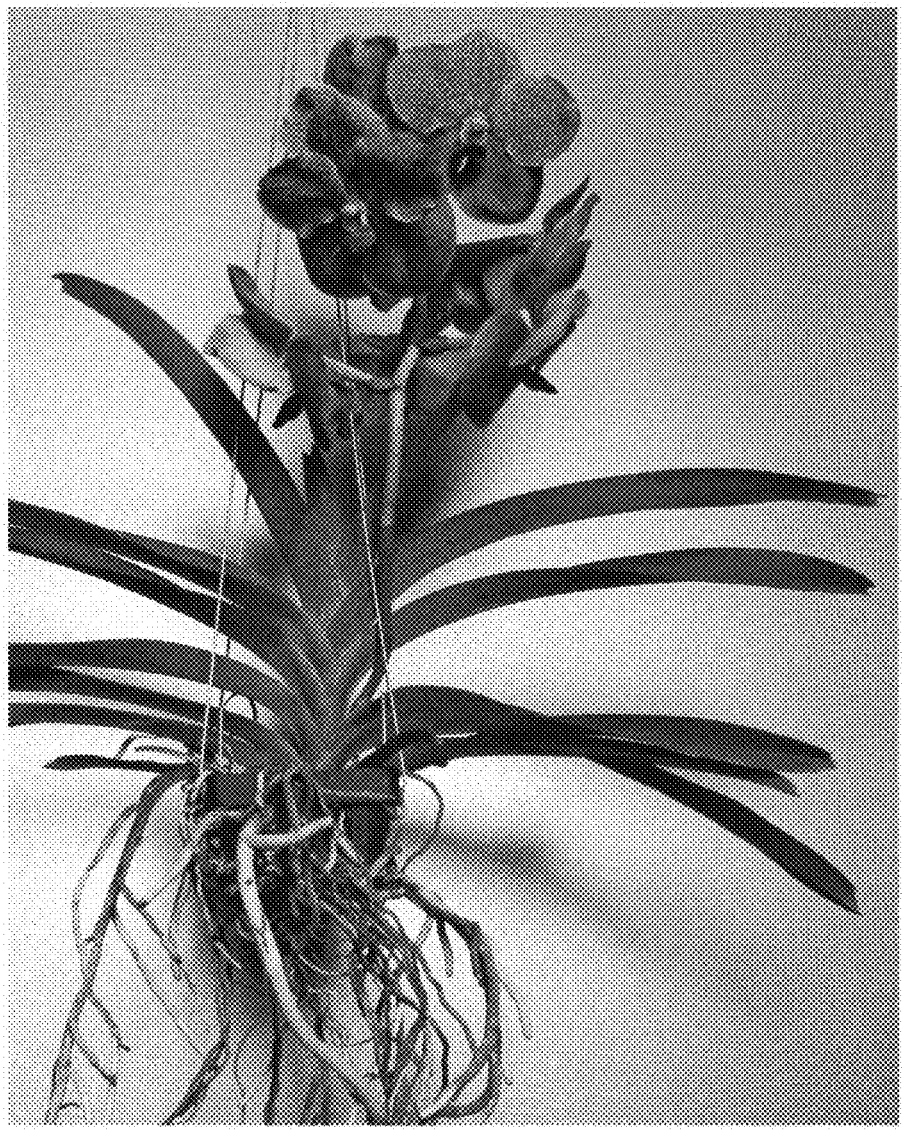

Latin name of the genus and species: *Vanda* hybrid.
Variety denomination: 'SPCDW1209'.

BACKGROUND OF THE INVENTION

This application relates to a new cultivar of *Vanda* hybrid and claims priority to EU application 2012/1963 filed Sep. 17, 2012. The new variety is the product of a planned breeding program. The new variety originated as a seedling from the crossing of the unpatented, proprietary seed parent *Vanda* 'ON137' with the unpatented, proprietary pollen parent referred to as *Vanda* 'NCMVN'. The crossing was made by the inventor in his research greenhouse in Chonburi, Thailand in August of 2001.

The new variety was first selected by the inventor, Thumrong Suphachadiwong, a citizen of Thailand, in September of 2006 in a research greenhouse belonging to the inventor in Chonburi, Thailand. After identifying the new variety as a potentially interesting selection, the inventor continued confidential testing and propagation of 'SPCDW1209', assessing stability of the unique characteristics of this variety.

Asexual reproduction of the new cultivar 'SPCDW1209' was first performed at a commercial laboratory belonging to the inventor in Chonburi, Thailand by tissue culture (propagation was performed using the base of leaves) in December of 2006. Access to all plants was restricted, as plants were kept in a greenhouse not open to the public, and tissue culture plantlets were in a laboratory belonging to the inventor, and not accessible to the public. Through subsequent propagation, multiple generations have been reproduced, which have shown that the unique features of this cultivar are stable and reproduced true to type.

SUMMARY OF THE INVENTION

The cultivar 'SPCDW1209' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SPCDW1209.' These characteristics in combination distinguish 'SPCDW1209' as a new and distinct *Vanda* cultivar:

1. Unique grey-orange colored flower with dark spots.
2. Bright green foliage.

PARENT COMPARISON

Plants of the new cultivar 'SPCDW1209' are similar to the seed parent, *Vanda* 'ON137' in most horticultural characteristics. However the new variety, 'SPCDW1209' differs from 'ON137' in the following characteristics:

1. Smaller flowers than parent.

Plants of the new cultivar 'SPCDW1209' are similar to the pollen parent, *Vanda* 'NCMVN' in most horticultural characteristics. However the new variety, 'SPCDW1209' differs from 'NCMVN' in the following characteristics:

1. Brighter flower color than parent.

COMMERCIAL COMPARISON

'SPCDW1209' is similar in most horticultural characteristics to the unpatented commercial variety *Vanda* 'SPCDDW1108' in most horticultural characteristics. However the new variety, 'SPCDW1209' differs from 'SPCDDW1108' in the following characteristics:

1. Flower color is grey-orange with brown spots. Comparator flower color is purple with dark purple spots.
2. Different lip shape.
3. Thinner column.

BRIEF DESCRIPTION OF THE PHOTOGRAPHS

The accompanying photograph in FIG. 1 illustrates in full color a typical plant of 'SPCDW1209' grown in a commercial greenhouse in Honselersdijk, the Netherlands. The plant is 5½ to 6½ years old, growing in a hanging basket without soil.

Figure 2:
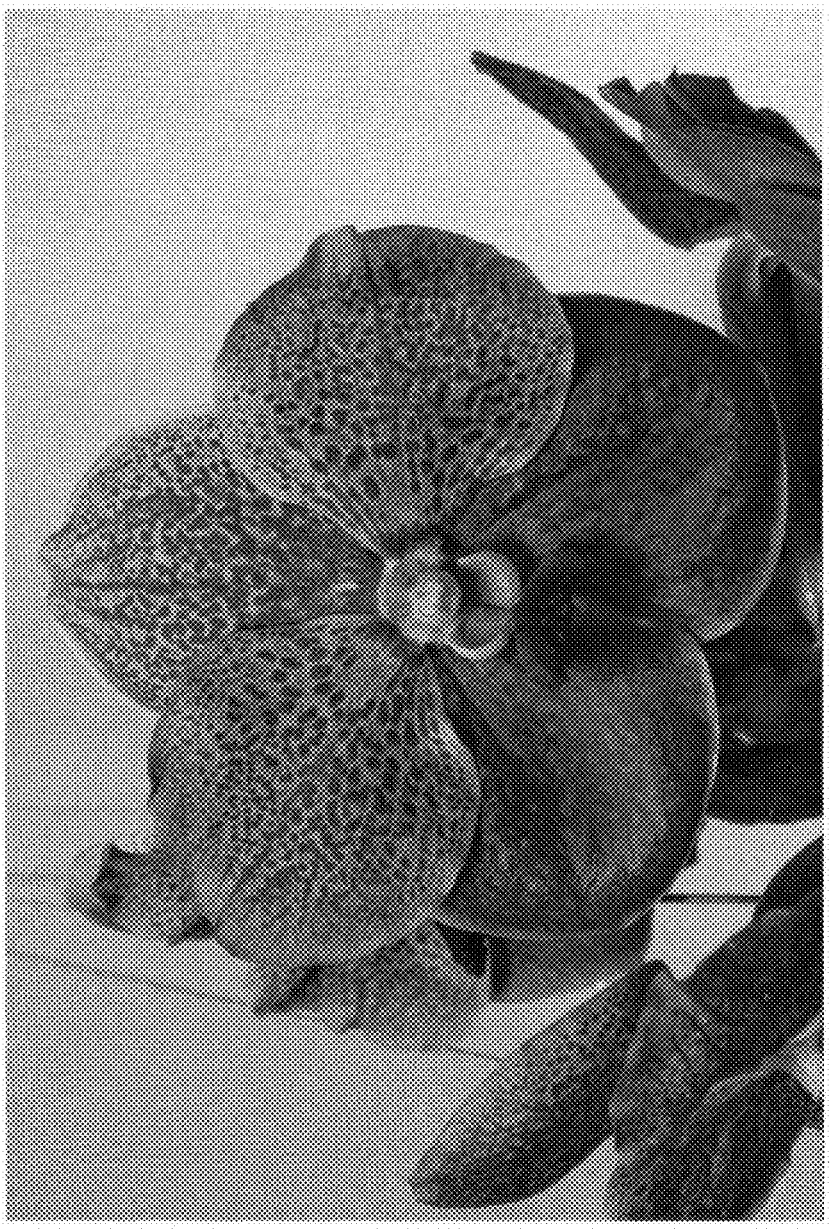

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'SPCDW1209' plants grown in a commercial greenhouse in Honselersdijk, the Netherlands. The plant is 5½ to 6½ years old. Described plant not container-grown, but in a hanging basket without soil. Temperatures ranged between 19° C. and 23° C. day and night. No photoperiodic or chemical treatments were given to the plants. During bright Summer conditions, shade was given. During dark Winter months, no supplemental light was given. Measurements and numerical values represent averages of typical plant types.

Botanical classification: *Vanda* hybrid 'SPCDW1209'.

PROPAGATION

Type of propagation typically used: Tissue culture propagation was performed using the base of leaves.

Time to produce a rooted cutting/liner: The time needed from for the start of a mericlone to get the small plants ready for deflasking is approximately 24 months under a controlled temperature of about 26 degrees Celsius. After that period they have matured roots. They start to make roots in the last 6 months in flasks. After deflasking they remain in the shadow under local outdoor temperatures.

Root description: Moderately to heavy rooting with aerial roots only. Roots very fleshy, non-fibrous. Average length of old roots: 52.4 cm, average diameter of old roots (mature, but ineffective): 0.2 mm, average diameter of young roots (mature, vital): 0.4 cm. Old roots colored yellow-green; near RHS 147B. Young roots colored greyed-green; near RHS 192C and 192D, growing tips of roots yellow-green; 152A. The roots are located at the base of the stem, growing from approx. the lowest 20% of the stem.

PLANT

Growth habit: Monopodial, upright.

Height from soil line to top of foliage: Average height from base (plant grown in hanging basket, so no soil line present) to top of foliage: 42.5 cm.

Height from soil line to top of flowers: Average height from base (plant grown in hanging basket, so no soil line present) to top of flowers: 52.0 cm.

Plant spread: Average: 53.8 cm.

Normal pot size: Hanging basket (8×8 cm square).

Growth rate: Moderate.

Number of leaves per plant: Average: 20.

FOLIAGE

Leaf:

- *Arrangement.*—Distichous.
- *Average length.*—Approximately 27.8 cm.
- *Average width.*—Approximately 2.9 cm.
- *Shape of blade.*—Ligulate, strongly carinate.
- *Aspect.*—Slightly curved.
- *Apex.*—Unequal praemorse.
- *Base.*—Sheathing. Sheath length: Average 2.6 cm. Sheath width: Average 1.5 cm. Sheath color: Green; near RHS 143B.
- *Margin.*—Entire.
- *Texture of top surface.*—Glabrous, very slightly glossy.
- *Texture of bottom surface.*—Glabrous, matte.
- *Color.*—Young foliage upper side: Green; near RHS 143A. Young foliage under side: Yellow-green; near RHS 144A. Mature foliage upper side: Green to greyed-green; a color in between near RHS 139A and N189A. Mature foliage under side: Yellow-green; near RHS 146A.
- *Venation.*—Type: Parallel. Venation coloration: As leaf surface; upper side: green to greyed-green; in between RHS 139A and N189A, lower side: yellow-green; near RHS 146A.

Petiole: No petioles present, leaves sessile.

FLOWERING CHARACTERISTICS

Flower bud:

- *Rate of opening.*—Buds open approx. three weeks from first sight.
- *Length.*—Average: 1.7 cm.
- *Diameter.*—Average: 1.6 cm.
- *Shape.*—Near globular to deltoid.
- *Color.*—Yellow-green; near RHS 145A, dotted greyed-purple; near RHS 185C and 185D.
- *Lastingness of flower* (*from open until it falls off*).—6 weeks.
- *Orientation.*—Outwards, towards all directions.

Peduncle:

- *Length.*—Approximately 40.5 cm.
- *Width.*—Approximately 0.7 cm.
- *Aspect.*—Approximately 30° angle to rosette.
- *Strength.*—Strong.
- *Texture.*—Smooth, moderately glossy.
- *Color.*—Green; near RHS 143A.

Inflorescence:

- *Flowers per stem.*—Average: 13.
- *Average stem diameter.*—1.2 cm.
- *Inflorescence arrangement.*—Axially placed raceme.
- *Inflorescence height.*—Approximately 25.5 cm (measured from base of lowest flower to top of upper flower).
- *Inflorescence width.*—Approximately 18.1 cm.
- *Inflorescence orientation.*—Obliquely upward.

Individual flowers:

- *Flower type.*—Zygomorphic (orchidaceous), typical shape for the genus *Vanda*.
- *Shape.*—Zygomorphic, consisting of three sepals and three petals, one of which is transformed into a labellum (lip).
- *Length* (*height*).—Approximately 8.3 cm.
- *Width.*—Approximately 9.3 cm.
- *Depth.*—Approximately 3.3 cm.
- *Fragrance.*—No fragrance.
- *Persistent.*—No.
- *Quantity of petals.*—3 (2 "traditional" petals and a labellum (lip), described separately).

Petals:

*Arrangement.*—One lateral petal on each side.

*Length.*—Approximately 4.4 cm.

*Width.*—Approximately 4.3 cm.

*Shape.*—Near orbicular to broad ovate.

*Apex.*—Obtuse.

*Base.*—Cuneate.

*Margin.*—Entire, slightly undulate.

*Texture.*—Upper forward surface: Glabrous, matte, velvety.

*Texture.*—Lower back surface: Glabrous, matte, velvety.

*Color.*—When opening, forward surface: Greyed-yellow; near RHS 160C and 160D, greyed-orange towards the margins and apex (the top of the lateral petal is located opposite the base of the petal); near RHS N170D and 177D, base greyed-red; 178B, petal heavily dotted greyed-purple; near RHS 183B and 183C. When opening, back surface: Greyed-green; near RHS 196C and 196D, greyed-red towards the margins and apex (the top of the lateral petal is located opposite the base of the petal); near RHS 182D, slightly dotted greyed-purple; near RHS 183D. Fully Opened, forward surface: Greyed-yellow to greyed-orange; near RHS 160C, 161A and 174C to 174D, base greyed-red; 178B, petal heavily dotted greyed-purple; near RHS 183B and 183C. Fully Opened, back surface: Greyed-green; near RHS 195B and 195C, greyed-red towards the margins and apex (the top of the lateral petal is located opposite the base of the petal); near RHS 182C and 182D, slightly dotted greyed-purple; near RHS 183D. Fading, forward surface: Greyed-red; near RHS 179C and 179D, heavily dotted greyed-purple; near RHS 185B. Fading, back surface: Greyed-orange; near RHS 173D, greyed-red towards the margins and apex (the top of the lateral petal is located opposite the base of the petal); near RHS 180C and 180D, slightly dotted darker; near RHS 180A and 180B.

*Color venation fully opened, forward surface.*—Main vein greyed-purple; near RHS 184B, other veins are not visible as such but colored as the forward surface. In parts where the surface color is 160C, the veins are also; in parts where the surface color is 161A, the veins are also; in parts where the surface color is 174C, the veins are also; in parts where the surface color is 174D, the veins are also; in parts where the surface color is 178B, the veins are also; in parts where the surface color is 183B, the veins are also; in parts where the surface color is 183C, the veins are also.

*Color venation fully opened, back surface.*—Main vein greyed-red; near RHS 182D, other veins are not visible as such but colored as the back surface. In parts where the surface color is 195B, the veins are also; in parts where the surface color is 195C, the veins are also; in parts where the surface color is 182C, the veins are also; in parts where the surface color is 182D, the veins are also; in parts where the surface color is 183D.

Labellum/lip:

*Shape.*—Three-lobed, lateral lobes involute, central lobe slightly revolute.

*Length.*—Approximately 2.0 cm.

*Width.*—Approximately 1.7 cm.

*Texture.*—Glabrous, slightly glossy, with 3 callosities.

*Central lobe.*—Praemorse tip (apex).

*Lateral lobes.*—Obtuse tips (apices).

*Base* (*where the central lobe is attached to the spur*).—Cuneate.

*Labellum.*—Lateral lobe length: Approximately 0.8 cm. Lateral lobe width: Approximately 0.8 cm. Central lobe length: Approximately 2.0 cm. Central lobe width: Approximately 1.7 cm.

*Color.*—When opening, forward surface: Lateral lobes yellow; near RHS 8D, striped greyed-red; near RHS 182D. Central lobe and callosities greyed-purple; near RHS 187D, base lighter; near RHS 184C, the apex of the central lobe of the labellum is much darker; near RHS N186C. When opening, back surface: Lateral lobes yellow; near RHS 11D, striped greyed-red; near RHS 182D. Central lobe greyed-purple; near RHS 184C, upper half darker; near RHS 187B. Fully Opened, forward surface: Lateral lobes yellow; near RHS 8D, striped greyed-red; near RHS 182D. Central lobe and callosities greyed-purple; near RHS 187D, base lighter; near RHS 184C, the apex of the central lobe of the labellum is much darker; near RHS N186C. Fully Opened, back surface: Lateral lobes yellow; near RHS 11D, striped greyed-red; near RHS 182D. Central lobe greyed-purple; near RHS 184C, upper half darker; near RHS 187A. Fading, forward surface: Not fading. Fading, back surface: Not fading. Color Venation Fully Opened, forward surface: No venation visible on labellum. Color Venation Fully Opened, back surface: No venation visible on labellum.

*Margin.*—Central lobe: entire. Lateral lobes: entire.

Spurs:

*Quantity.*—Average: 1.

*Appearance.*—Short triangular, in line with central lobe of labellum.

*Length.*—Approximately 0.7 cm.

*Width.*—Approximately 0.3 cm.

*Height.*—Approximately 0.7 cm (at the base).

*Shape.*—Short triangular.

*Apex.*—Obtuse.

*Base.*—Broad cuneate.

*Margin.*—Entire.

*Texture.*—Glabrous, slightly glossy.

*Color.*—White; near RHS N155C, striped greyed-purple; near RHS 186D.

*Type.*—Short triangular.

Sepals:

*Quantity.*—Average: 3.

*Appearance.*—One dorsal sepal (pointing upright) and two lateral sepals.

*Length.*—Dorsal sepal approximately 4.4 cm. Lateral sepals approximately 4.3 cm.

*Width.*—Dorsal sepal approximately 4.4 cm. Lateral sepals approximately 5.1 cm.

*Shape.*—Broad ovate to near orbicular.

*Apex.*—Obtuse.

*Base.*—Cuneate.

*Margin.*—Entire.

*Texture.*—Glabrous, matte, velvety.

*Color.*—Dorsal sepal upper side: Greyed-yellow; 160A to 160B, greyed-orange towards the top; near RHS 174D and 177D, sepal heavily dotted greyed-purple; 183B to 183C. Dorsal sepal under side: Greyed-red; 178C, tinged greyed-orange; 165C dotted darker near the margins; 178A. Lateral sepal upper side: Greyed-purple; 187B to 187C, base slightly dotted greyed-yellow; 161A. Lateral sepal under side: Greyed-orange; 176A, 176B and 177B and 177C.

Pedicels:

*Length.*—Approximately 5.2 cm.

*Diameter.*—Approximately 0.6 cm.

*Angle.*—Approximately 65° angle to peduncle.

*Strength.*—Very strong.

*Texture.*—Glabrous, axially angled with 5 "ribs", axially twisted (due to resupination), glossy.

*Color.*—Greyed-purple; near RHS 186B, 186C and 186D.

REPRODUCTIVE ORGANS

*Stamens, style and stigma fused into column?.*—Yes.

*Column length.*—Approximately 0.7 cm.

*Column diameter.*—Approximately 0.6 cm.

*Column color.*—Yellow-green; near RHS 150C and 150D.

*Ovary.*—Position: Inferior. Diameter: Approximately 0.5 cm. Color: White; near RHS 155A.

*Pollinia color.*—Yellow-orange; near RHS 14A.

OTHER CHARACTERISTICS

Disease resistance: Neither resistance nor susceptibility to the normal diseases found in *Vanda* has been observed.

Drought tolerance and cold tolerance: Normal for species.

Fruit/seed production: No fruits/seeds detected to date.

What is claimed is:

1. A new and distinct cultivar of *Vanda* plant named 'SPCDW1209' as herein illustrated and described.

* * * * *